(12) United States Patent
Gateshki et al.

(10) Patent No.: US 10,352,881 B2
(45) Date of Patent: Jul. 16, 2019

(54) COMPUTED TOMOGRAPHY

(71) Applicant: MALVERN PANALYTICAL B.V., Almelo (NL)

(72) Inventors: Milen Gateshki, Almelo (NL); Detlef Beckers, Almelo (NL)

(73) Assignee: MALVERN PANALYTICAL B.V., Almelo (NL)

( * ) Notice: Subject to any disclaimer, the term of this patent is extended or adjusted under 35 U.S.C. 154(b) by 164 days.

(21) Appl. No.: 15/391,356

(22) Filed: Dec. 27, 2016

(65) Prior Publication Data

US 2018/0180560 A1 Jun. 28, 2018

(51) Int. Cl.
*G01N 23/046* (2018.01)

(52) U.S. Cl.
CPC ..... *G01N 23/046* (2013.01); *G01N 2223/309* (2013.01); *G01N 2223/419* (2013.01); *G01N 2223/501* (2013.01)

(58) Field of Classification Search
CPC .......... G01N 23/046; G01N 2223/309; G01N 2223/419; G01N 2223/501
See application file for complete search history.

(56) References Cited

U.S. PATENT DOCUMENTS

2013/0251100 A1\* 9/2013 Sasaki ................. G01N 23/046
378/20

\* cited by examiner

*Primary Examiner* — Courtney D Thomas
(74) *Attorney, Agent, or Firm* — Leason Ellis LLP

(57) ABSTRACT

Apparatus for computed tomography is described that is also suitable for X-ray diffraction. The computed tomography measurement uses a line focus 8 and passes the X-rays from the line focus through a perpendicular slit 22 and then through a sample onto a two dimensional detector. A plurality of images are taken, each with the sample rotated about a rotation axis 14 by a different amount, and combined to create a computed tomography image.

11 Claims, 6 Drawing Sheets

COMPUTED TOMOGRAPHY

FIELD OF INVENTION

The invention relates to a method of carrying out computed tomography in apparatus also carrying out conventional X-ray diffraction measurements, as well as corresponding methods and software.

BACKGROUND TO THE INVENTION

Computed tomography, CT, is a technique for building up a computed three dimensional image from multiple input images. The technique is widely used in medicine. However, the cost of apparatus used for medical computed tomography is very high. The technique is also used in industrial applications but the high cost of the apparatus limits its use There would therefore be a benefit in apparatus capable of producing computed tomography images as well as carrying out other tasks which may need X-rays, for example X-ray diffraction or X-ray fluorescence, and in methods which may use such apparatus. In this way, X-ray equipment that may be needed in any event in an industrial or research setting can be used also for additional tomography. There is also a benefit in making it possible to switch the apparatus between a set up for computed tomography and a set up for other applications without requiring complete recalibration of the whole apparatus.

SUMMARY OF THE INVENTION

According to a first aspect of the invention there is provided a method of carrying out computed tomography measurements, comprising:
generating a beam of X-rays in an X-ray source;
creating a line focus of X-rays extending linearly in a first direction;
passing the beam of X-rays from the line focus though a mechanical slit in a mask, the mechanical slit extending in a slit direction substantially perpendicular to the line focus;
passing the beam of X-rays after passing through the mechanical slit through an object to be measured; and
imaging the beam of X-rays on a two dimensional detector.

The use of a line focus is conventional for in particular X-ray diffraction measurements. Therefore, by carrying out CT on a sample using a configuration in which the input X-rays originate from a line focus or are brought to a line focus it is possible to rapidly switch to carrying out X-ray diffraction using the same apparatus without requiring a extensive setting up and alignment of the line focus. Further, no special focussing optics for computed tomography are required.

Further, by using a line focus instead of a spot focus embodiments of the invention can deliver improved resolution with reasonable power—a very small spot size can also achieve good resolution but at the cost of a very low intensity and hence very long measurement times.

The method may in particular include rotating the object sequentially to a plurality of positions;
capturing a respective image on the two-dimensional detector for each of the plurality of positions; and
calculating a three-dimensional representation of the object from the respective two-dimensional images.

The inventors have realised that no conventional algorithm for carrying out the calculations for computed tomography is available to cope with the geometric arrangement proposed here.

In principle, it is possible to capture these images and carry out calculations. However, in general, the calculations for computed tomography are very complex and it is preferred to use one of a variety of conventional algorithms which have been optimised in order to be able to get reasonable output in a reasonable time.

The inventors have realised that in the case of the geometry proposed here it is possible to process the data in such a way that one such conventional algorithm can be used. In particular, conventional CT algorithms exist for calculating a three-dimensional image from a plurality of images captured from a point source passing through an object and recording the resulting image on a two-dimensional detector—such CT processes are known as cone beam CT. However, no such point source is present in the method described here. Therefore, the calculations cannot simply be carried out using conventional cone beam CT algorithms.

One example of such an algorithm is described in L. Feldkamp, L. Davis, and J. Kress, "Practical cone-beam algorithm," Journal of the Optical Society of America, vol. 1, no. 6, pp. 612-619, June 1984.

Accordingly, to convert the captured data to data that can be processed using convention cone beam computed tomography methods, the two-dimensional images may be scaled.

In particular, the method may include carrying out a cone beam computed tomography algorithm on an the captured two dimensional images with each captured image scaled in the direction parallel to the first direction relative to the direction perpendicular to the first direction by the scaling factor S to calculate the three-dimensional representation of the object.

S may be given by:

$$S=(d_{mo}/d_{so})(d_{ad}/d_{md});$$

$d_{mo}$ is the distance between the mask and the object;
$d_{so}$ is the distance between the line source and the object;
$d_{sd}$ is the distance between the line source and the detector; and
$d_{md}$ is the distance between the mask and the detector.
This scaling may be carried out In another aspect the invention relates to computed tomography measurement apparatus, comprising:
an X-ray source for generating a beam of X-rays;
an X-ray source generating a line focus in a first direction or an X-ray optic behind the X-ray tube that is creating a line focus of X-rays extending linearly in a first direction;
a sample stage for holding a sample to be measured;
though(?) a mechanical slit in a mask, the mechanical slit extending in a slit direction substantially perpendicular to the line focus; and
a two-dimensional detector for detecting X-rays from the X-ray source having passed through a sample on the sample stage and generating a two-dimensional image;
characterised by
a mask defining a mechanical slit extending in a slit direction substantially perpendicular to the line focus, the mask being mounted between the line focus and the sample stage directing X-rays from the line focus through the slit and then onwards through a sample on the sample stage to the two-dimensional detector to create the two-dimensional image.

The sample stage may be rotatable about a rotation axis, and the apparatus may further comprise: a computer system connected to the sample stage for controlling the rotation of the object and connected to the two-dimensional detector for processing the two-dimensional image; wherein the computer system is adapted: to rotate the sample stage to rotate the object sequentially to a plurality of positions; to capture a respective image on the two-dimensional detector for each of the plurality of positions; and to calculate a three-dimensional representation of the object from the respective two-dimensional images.

Note that references herein to "a computer system" may refer to a single computer with a single processor or to a network of computers connected together. In a particular embodiment, the computer system includes one computer used to control the rotation of the sample and a second computer which is used to calculate the three dimensional representation.

The rotation axis may be substantially perpendicular to the axis from the source to detector.

In a yet further aspect, the invention relates to a computer program product, recorded on a data carrier, wherein the computer program product is adapted when run on a computer system of the X-ray apparatus as described herein, to cause the X-ray apparatus to carry out a method as set out above.

The computer program product may be provided in separate parts to be run on respective computers.

BRIEF DESCRIPTION OF THE DRAWINGS

Embodiments of the invention will now be described with reference to the accompanying diagrams, in which.

The Figures are schematic and not to scale.

DETAILED DESCRIPTION

Figure 1:
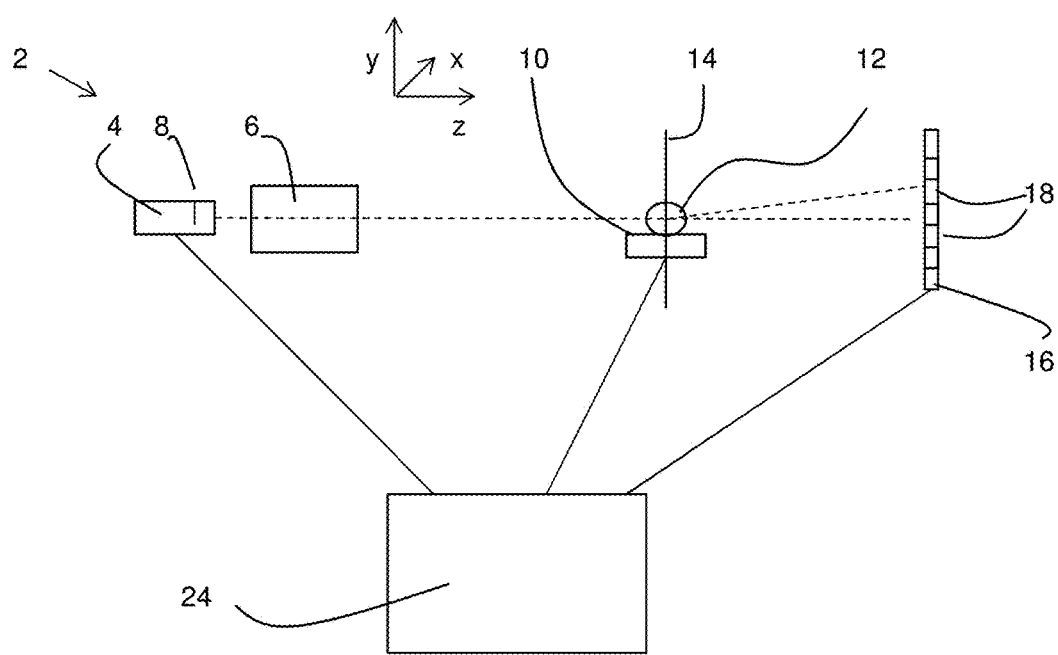
FIG. 1 illustrates X-ray apparatus for carrying out XRD measurements.
Figure 2:
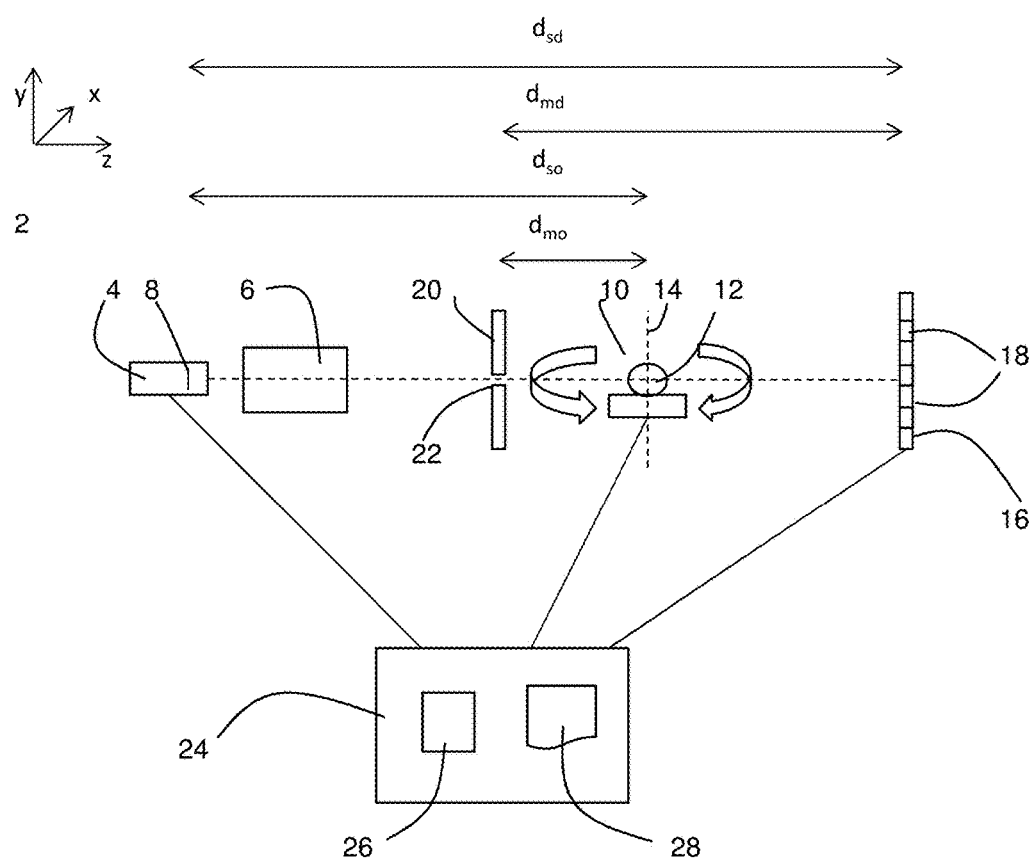
FIG. 2 illustrates an adaptation of the apparatus of FIG. 1 for carrying out CT measurements.

Referring to FIGS. 1 and 2, X-ray apparatus 2 includes an X-ray source 4 that generates a line focus 8 of X-rays. The X-rays all pass through a focal line or are generated from a focal line. The focal line extends in a first direction and with a width in a direction perpendicular to the first direction less than 2% of the length of the line focus.

Note that the effective size of the line focus can be less than the actual width of the X-ray line. The focal line in the X-ray tube used in the examples has a dimension 12 mm by 0.4 mm at the anode but this is used at an angle of approximately 6° when tuned to a line focus mode which reduces the effective focal dimension as seen by the sample by around a factor of 10. This means when the tube is used in line focus mode it delivers an effective focus size of 12 mm×0.04 mm and when it is turned to the point focus mode the tube focus is effectively 1.2 mm×0.4 mm.

Those skilled in the art will realise that other tubes with slightly different dimensions for example 8 mm×0.4 mm, 10 mm×1 mm or 12 mm×2 mm are available and that these generate an effective length:width ratio typically 40 to 500, typically in the range 60 to 300.

An optics module 6 is additionally provided. This may be for example a divergence slit module which determines the illuminated area on the sample in reflection Bragg-Brentano diffraction geometry, and optionally additionally Soller slits and a mask. For transmission geometery, as illustrated in FIG. 1, a very thin slit may be used.

To carry out computed tomography, as illustrated in FIG. 2, the optics 6 may also use the divergence slit module, large enough to illuminate sample and detector. The main function of this is to reduce the scatter and prevent X-rays from illuminating other parts in the instrument that can cause high background. Thus, this component does not need to be removed when switching the instrument between CT and other measurements.

However, any other components present in optics 6 such as Soller slits will in general need to be removed.

A sample holder 10 is provided that can hold a sample 12. The sample holder can be rotated along a rotation axis 14. It is not necessary that the rotation axis 14 is parallel to the line focus 8 as long as it is known since the reconstruction algorithms used (see below) can normally cope with non-parallel rotation axes.

A two dimensional detector 16, i.e. a detector having a two-dimensional array of pixels 18 is provided.

A controller 24 is provided connected to the X-ray source 4, sample holder 10 and detector 16 to control the apparatus 2 and to collect data. The controller includes a processor 26 as well as code 28 arranged to cause the controller to carry out the method as described below, in particular to carry out the computed tomography algorithm. In alternative embdoments the system control and data collection are on separate computers As illustrated in FIG. 1, the apparatus as described above may be a conventional X-ray diffraction apparatus in which the X-ray source 4, two-dimensional detector 16 and sample holder 10 are mounted on goniometers.

To carry out angle dependent X-ray diffraction, a sample 12 is mounted on the sample holder and the resulting diffraction pattern measured as a function of deflection angle (conventionally 2 θ) using the two dimensional detector. The detector can measure a certain range of angle 2 θ without being moved.

Figure 3:
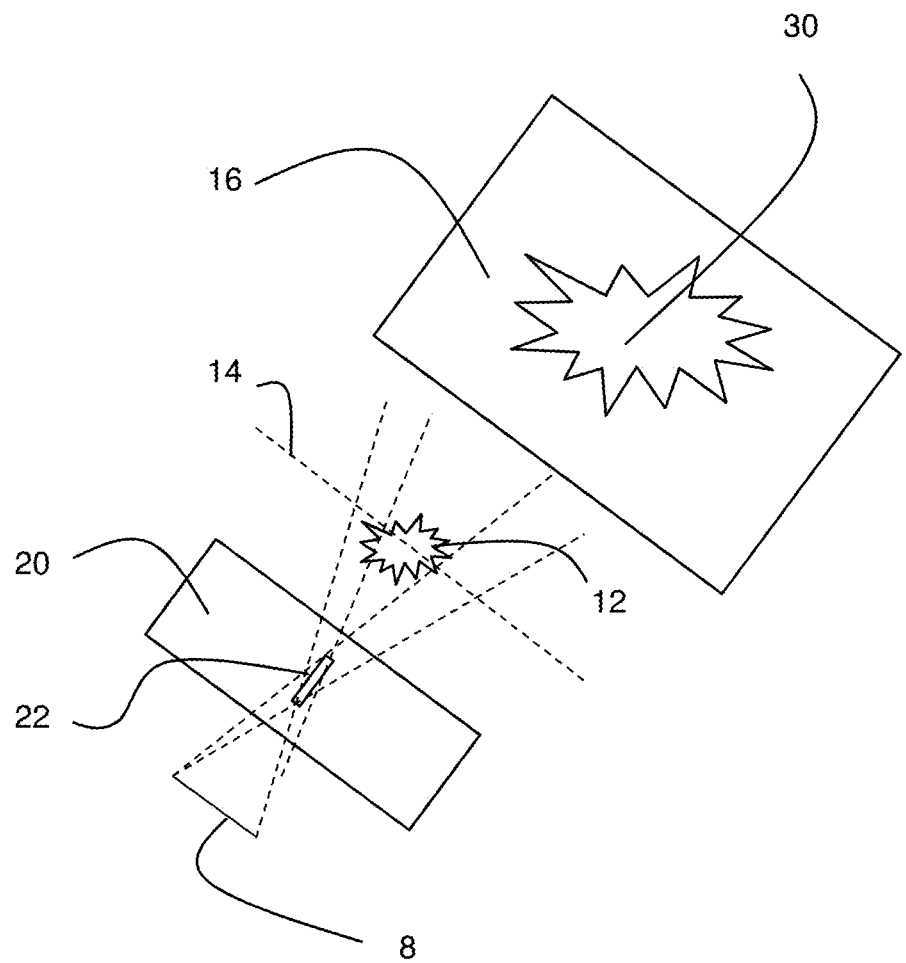
FIG. 3 illustrates in perspective view the arrangement of FIG. 2.

The same apparatus can also be used to carry out computed tomography measurements (CT measurements) as illustrated in FIGS. 2 and 3.

To do this, a mask 20 is introduced into the apparatus between the line focus 8 and the sample holder 10. The mask has a slit 22 which extends in a direction substantially perpendicular to the direction of the line focus, both extending substantially perpendicular to the X-ray beam direction. Thus, referring to the x, y and z axes shown in FIG. 2, the X-ray beam extends in the z direction (left to right in FIG. 2), the line focus in the y direction (top to bottom in FIG. 2) and the slit in the x direction (into the paper). This sets the apparatus up for the computed tomography measurements as will be explained below.

FIG. 3 is a perspective view showing the slit 22 extending in a direction essentially perpendicular to the line focus 8, to better illustrate the directions. FIG. 3 shows the image 30 created on the detector 16 from the X-rays originating from the line focus 8 and slit 22, then through the sample 12 onto the detector 16.

A sample 12 held in the sample holder 10 will be referred to alternatively as the object, to avoid confusion between the sample and the source in the formulae below, since both "sample" and "source" begin with the same letter.

Note, in the formulae below, the distances between the mask m, sample referred to as object o, and line source s are defined by:

$d_{mo}$ is the distance between the mask and the object;
$d_{so}$ is the distance between the line source and the object;
$d_{sd}$ is the distance between the line source and the detector; and
$d_{md}$ is the distance between the mask and the detector.

FIG. 2 is not to scale. In practice, the line focus 8 and the slit 22 will be relatively close to the object 12 and the two-dimensional detector 16 will be relatively far from the object.

The precise distances used will depend on several parameters: line focus dimension, mask size, object and detector size. Since the object is magnified towards the detector the first practical limit for the distance of the detector is its size: the image of the object has still to be smaller than the detector. The best position for high resolution depends on the pixel size of the detector and the focal dimensions (line focus width/mask width). If the detector pixels are smaller, the object should be closer to the detector: if the focus size is smaller the sample should be closer to the focus so that a magnification effect can be achieved. In the examples below the effective line focus width was 0.04 mm and the slit width in the mask 20 about 0.05 mm (mask) with detector pixels of size 0.055 mm×0.055 mm so a good sample position is close to the middle between detector and the averaged focus positions.

In practice the line focus 8 and the slit 22 are ideally relatively close to each other. To optimize resolution (parallel or perpendicular to the line focus), the distance to the object 12 and the two-dimensional detector 16 will—as in traditional CT scanners—depend on the focus and mask dimension as well as the detector pixel sizes.

In particular,—if mask and line focus width are similar to the pixel dimensions of the detector—the typical distances from sample to detector are between 0.3 and 3 times the distances between sample and mask, and the distance between the mask and the line focus are typically no greater than the distance between mask and sample.

To carry out CT measurements, a sample 12 is mounted, and a beam of X-rays from a line focus 8 is generated by the X-ray source 4. The beam is conditioned by the X-ray optics 6. The X-rays are then passed through the slit 22, the sample 12 mounted on the sample holder 10, and a first image of the sample is captured on the two-dimensional detector.

The sample 12 is then rotated by controller 24 about axis 14 and a further image of the sample 12 captured. This is repeated until a sufficient number of images at different rotations of the sample are captured.

The controller then calculates a computed tomography image from the plurality of images captured at different rotation axes.

The calculations for computed tomography are in general very complicated and the arrangement described here does not exactly correspond to any of the standard algorithms.

The inventors have realized that it is possible to scale the captured images to take into account the geometry in such a way that it is possible to use a conventional computed tomography algorithm, in particular a cone beam computed tomography algorithm, to carry out the calculations of the three-dimensional shape of the object. This makes it possible to use off-the-shelf algorithms which is highly desirable in view of the complexity of such calculations and algorithms.

To scale the captured image, each image is scaled by a factor S in the direction parallel to the line focus, the y direction which is the axial direction. S is given by:

$$S=(d_{mo}/d_{so})(d_{ad}/d_{md});$$

The image is not scaled in the equatorial direction, the x direction which is the lengthwise direction of the slit 22.

It will be appreciated by those skilled in the art that the important thing is the scaling in the y direction relative to the scaling in the x direction. Thus, instead of scaling the captured image in the y direction by the factor S, the image can instead be scaled in the x direction by the factor (1/S) which leads to the same relative scaling between x and y directions.

One option is to scale the y direction by a factor S and leave the x-direction unscaled. In this case, the position of the line focus may be used as a virtual point focus position in the CT reconstruction algorithm.

Another option is to scale the x direction by a factor 1/S and the leave y-direction unscaled. In this case the mask position is used as virtual point focus position in the CT reconstruction algorithm to get the correct dimensions in the 3D image.

Note that in practice the scaling can be carried out in a variety of ways. In some cases, the software used to carry out the computed tomography algorithm may have inputs related to the pixel size in each direction, so in this case the scaling can be carried out by inputting a pixel size that is corrected by the factor S in one dimension. For example, the detector may actually have pixels with the physical size of 55 μm×55 μm but the scaling may be carried out by inputting instead a pixel size of 40 μm×55 μm. Alternatively, the images may be scaled by a separate scaling algorithm before inputting the image into the computed tomography algorithm. Another possibility is to scale the reconstructed 3D image after applying the computed tomography algorithm, but in this case the scaling would need to be a two-dimensional scaling.

Experiments were carried out using a PANalytical X'Pert apparatus usually used for X-ray diffraction.

The line focus of the X-ray source had an effective width of 0.04 mm and the slit in the mask had a width of 0.04 to 0.05 mm. The two-dimensional detector had a pixel size of 0.055 mm by 0.055 mm.

Cone beam computed tomography was carried out as a comparative example without using the line focus or the slit but simply using the source in point focus with an effective focus size 1.2 mm×0.4 mm as a source of X-rays and rotating the object. The resolution obtained was 60 to 100 μm.

Using the combination of line focus and slit reduced the resolution down to around 40 μm.

It was discovered that the effective brightness varied over the two dimensional pixel detector, i.e. that the image was not flat field. To correct for this, a flat field image was taken with no sample present and used to correct for the brightness across the image with a sample present by scaling the measured intensity by the reciprocal of the measured intensity in the flat field image.

Figure 4:
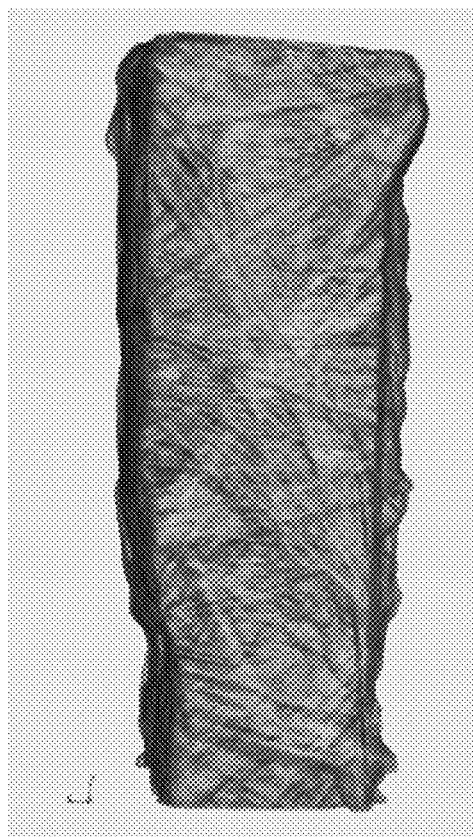
FIG. 4 is a comparison between CT measurements made without and with the invention.
Figure 4:
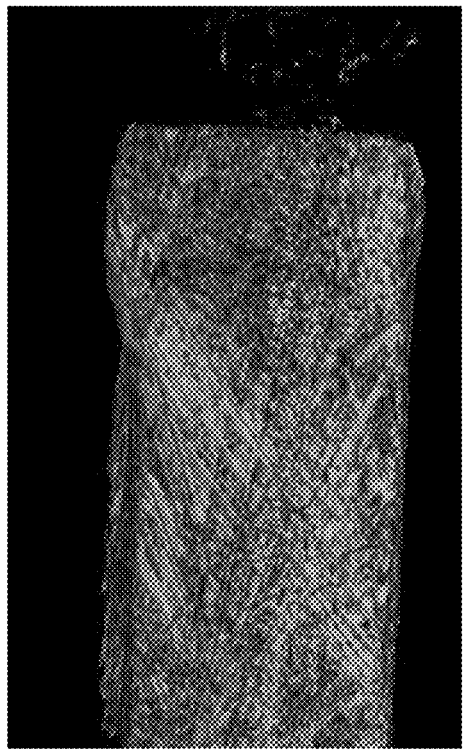

FIG. 4 shows results of a glass fiber composite sample using a copper source. The left image is taken without using the line focus or slit, and the right image shows the effect of using the combination of line focus and slit. The time to optimize the reconstruction was much faster using the combination of line focus and slit. Since the normal point focus set-up could only just resolve the fibers, the reconstruction and image processing was more difficult and time consuming and required a lot of manual optimization work was required. In contrast, using the invention the better resolution meant that additional optimization was not required. The required power was higher (600-1500 W instead of 100-200 W) but such a power is conventionally available with a line focus tube set up conventionally used for X-ray diffraction measurements.

Figure 5:
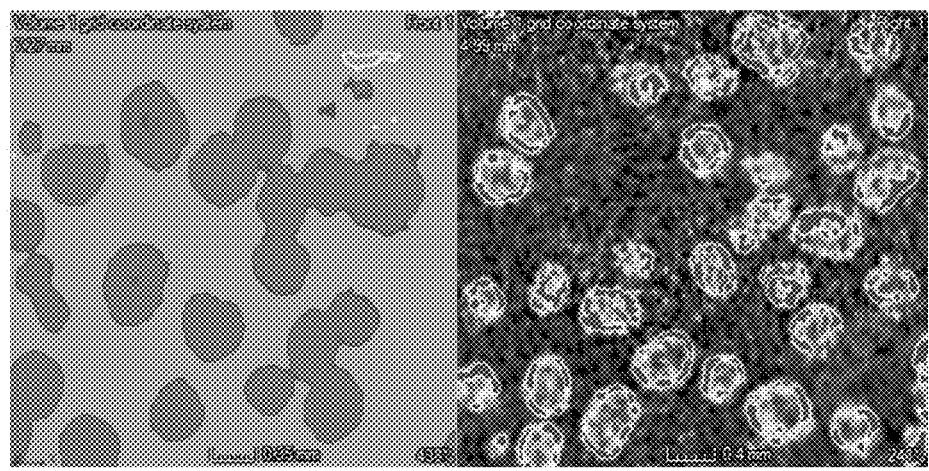
FIG. 5 is a comparison between CT measurements made without and with the invention.

Using a molybdenum source, similar results were obtained as illustrated in FIG. 5 showing measurements on a Nexium® MUPS 20 mg tablet sample (AstraZeneca). Again, the left image is without the line focus or slit, and the right image shows improved resolution with the line focus or slit.

A further benefit of using the invention is that all that is required of the sample stage is that it is able to rotate the sample in a controlled way (Note: what I mean is that the sample rotation angle has to be known for each 2D image). Such sample stages are readily available for X-ray diffraction.

In addition to higher resolution measurements using the line focus and slit, the use of the line focus allows the apparatus to be quickly and easily used for both conventional Bragg-Brentano XRD and CT measurements since it is not necessary to rotate or change the source, which is a time consuming process, every time that the apparatus is switched between CT and XRD measurements. Instead, the same line focus can be used for both.

The magnification and resolution are effectively selected by the distance from line focus and slit to the sample and the sample to the detector. Accordingly, by varying these distances different magnifications and resolutions can be obtained.

Figure 6:
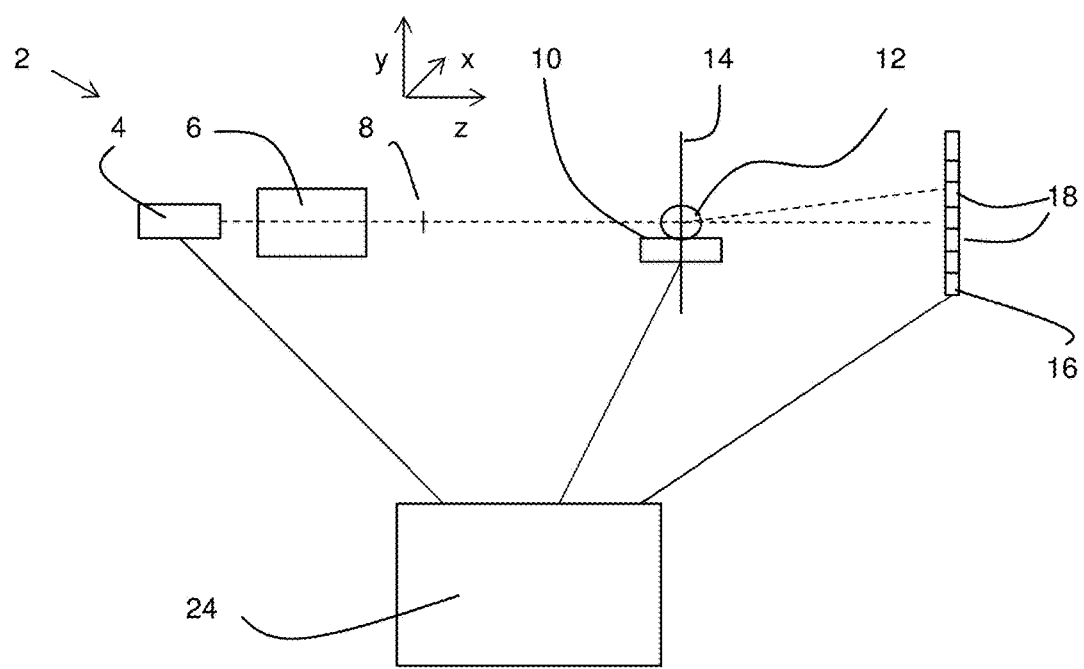
FIG. 6 illustrates an alternative X-ray apparatus.

In the arrangement of FIG. 1, the line focus is provided by the X-ray tube. In another embodiment, illustrated in FIG. 6, the line focus 8 is defined by X-ray focussing optics 6. The same method applies, but in this case separate components generate the line focus. Note that the X-ray focussing optics may be set up once, for both CT and conventional measurements, and the same line focus used for both measurements.

The invention claimed is:

1. A method of carrying out computed tomography measurements, comprising:
   generating a beam of X-rays in an X-ray source;
   creating a line focus of X-rays extending linearly in a first direction;
   passing the beam of X-rays from the line focus though a mechanical slit in a mask, the mechanical slit extending in a slit direction substantially perpendicular to the line focus;
   passing the beam of X-rays after passing through the mechanical slit through an object to be measured; and
   imaging the beam of X-rays on a two dimensional detector.

2. A method according to claim 1, comprising:
   rotating the object sequentially to a plurality of positions;
   capturing a respective image on the two-dimensional detector for each of the plurality of positions; and
   calculating a three-dimensional representation of the object from the respective two-dimensional images.

3. A method according to claim 2, wherein calculating a three-dimensional representation of the object comprises carrying out a cone beam computed tomography algorithm on the captured two dimensional images with each captured image scaled in the direction parallel to the first direction relative to the direction perpendicular to the first direction by a scaling factor S.

4. A method according to claim 3, wherein the scaling factor, S, is given by:

$$S=(d_{mo}/d_{so})(d_{sd}/d_{md});$$

$d_{mo}$ is the distance between the mask and the object;
$d_{so}$ is the distance between the line source and the object;
$d_{sd}$ is the distance between the line source and the detector; and
$d_{md}$ is the distance between the mask and the detector.

5. A method according to claim 1 wherein the X-ray source uses a target of a metal element having an atomic number in the range 24 to 47 and has a power from 600 to 3000 W.

6. Computed tomography measurement apparatus, comprising:
   an X-ray source for generating a line focus extending linearly in a first direction;
   a sample stage for holding a sample to be measured; and
   a two-dimensional detector for detecting X-rays from the X-ray source having passed through a sample on the sample stage and generating a two-dimensional image; and
   a mask defining a mechanical slit extending in a slit direction substantially perpendicular to the line focus, the mask being mounted between the line focus and the sample stage directing X-rays from the line focus through the slit and then onwards through a sample on the sample stage to the two-dimensional detector to create the two-dimensional image.

7. Computed tomography measurement apparatus according to claim 6,
   wherein the sample stage is rotatable about a rotation axis,
   the apparatus further comprising: a computer system connected to the sample stage for controlling the rotation of the object and connected to the two-dimensional detector for processing the two-dimensional image;
   wherein the computer system is adapted:
      to rotate the sample stage to rotate the object sequentially to a plurality of positions;
      to capture a respective image on the two-dimensional detector for each of the plurality of positions; and
      to calculate a three-dimensional representation of the object from the respective two-dimensional images.

8. Computed tomography measurement apparatus according to claim 7, wherein the computer system is adapted:
   to calculate a three-dimensional representation of the object by carrying out a cone beam computed tomography algorithm on the captured two dimensional images with each captured image scaled in the direction parallel to the first direction relative to the direction perpendicular to the first direction by a scaling factor, S.

9. Computed tomography measurement apparatus according to claim 8, wherein
   the scaling factor, S, is given by:

$$S=(d_{mo}/d_{so})(d_{sd}/d_{md});$$

$d_{mo}$ is the distance between the mask and the object;
$d_{so}$ is the distance between the line source and the object;
$d_{sd}$ is the distance between the line source and the detector; and
$d_{md}$ is the distance between the mask and the detector.

10. Computed tomography measurement apparatus according to claim 6 wherein the X-ray source comprises a target of a metal element in the range Chromium to Silver.

11. A computer program product, recorded on a data carrier, for controlling computed tomography measurement apparatus comprising an X-ray source for generating a line focus extending linearly in a first direction; a sample stage rotatable about a rotation axis for holding a sample to be measured; a two-dimensional detector for detecting X-rays from the X-ray source having passed through a sample on the sample stage and generating a two-dimensional image; and a mask defining a mechanical slit extending in a slit direction substantially perpendicular to the line focus, the mask being mounted between the line focus and the sample stage directing X-rays from the line focus through the slit and then onwards through a sample on the sample stage to the two-dimensional detector to create the two-dimensional image;

wherein the computer program product is adapted to control the computed tomography measurement apparatus:

to rotate the sample stage to rotate the sample sequentially to a plurality of positions;

to capture a respective image on the two-dimensional detector for each of the plurality of positions; and to calculate a three-dimensional representation of the sample from the respective two-dimensional images.

\* \* \* \* \*